United States Patent [19]
Davis et al.

[11] Patent Number: 5,733,275
[45] Date of Patent: Mar. 31, 1998

[54] INTEGRALLY BELTED ABSORBENT PRODUCTS

[75] Inventors: Martha Davis, New York, N.Y.; Daniel Formosa, Montvale, N.J.; Jeannie Gerth, Philadelphia, Pa.; Patricia A. Moore, Montvale; Stephen Russak, Hoboken, both of N.J.; Tamara Thomsen; Tucker A. Viemeister, both of New York, N.Y.; Nels J. Lauritzen, Piscataway, N.J.

[73] Assignee: McNeil-PPC, Inc., Skillman, N.J.

[21] Appl. No.: 735,158

[22] Filed: Oct. 22, 1996

Related U.S. Application Data

[63] Continuation of Ser. No. 431,528, May 1, 1995, abandoned, which is a continuation of Ser. No. 116,104, Sep. 2, 1993, abandoned, which is a continuation of Ser. No. 976,284, Nov. 9, 1992, abandoned, which is a continuation of Ser. No. 849,806, Mar. 11, 1992, abandoned, which is a continuation of Ser. No. 715,871, Jun. 14, 1991, abandoned, which is a continuation of Ser. No. 549,330, Jul. 6, 1990, abandoned.

[51] Int. Cl.$^6$ ........................................ A61F 13/15
[52] U.S. Cl. ........................................ 604/387; 604/392
[58] Field of Search ........................................ 604/386, 387, 604/392, 393, 396

[56] References Cited

U.S. PATENT DOCUMENTS

| 4,560,380 | 12/1985 | Tharel | 604/392 |
| 4,909,802 | 3/1990 | Ahr et al. | 604/392 |

*Primary Examiner*—John G. Weiss
*Assistant Examiner*—Dennis Ruhl

[57] ABSTRACT

Absorbent products having integral belt means for retaining the absorbent product in a position to absorb body fluids are disclosed. In a preferred embodiment, a napkin is provided wherein straps are cut from the material of the napkin. These straps are then tied around the body of the user when the napkin is applied. The straps are flexible enough to allow them easily to be tied to each other on the side. The straps may or may not be retained by the waistband of an undergarment. Alternatively, a second embodiment is provided wherein long flap-like straps extend longitudinally away from the transverse ends of the absorbent product. These straps are then engaged by the elastic waistband on an undergarment, to retain the napkin in place. Methods of manufacturing absorbent products are also disclosed.

9 Claims, 5 Drawing Sheets

INTEGRALLY BELTED ABSORBENT PRODUCTS

CROSS-REFERENCE TO RELATED APPLICATIONS

This is a continuation application of Ser. No. 08/431,528 filed May 1, 1995 now abandoned which is a continuation of Ser. No. 08/116,104 filed Sep. 2, 1993, now abandoned which is a continuation of Ser. No. 07/976,284, filed Nov. 9, 1992, now abandoned which is a continuation of Ser. No. 07/849,806, filed Mar. 11, 1992, now abandoned which is a continuation of Ser. No. 07/715,871, filed Jun. 14, 1991, now abandoned which is a continuation of Ser. No. 07/549,330, filed Jul. 6, 1990, now abandoned all of which are herein incorporated by reference.

The present invention relates to absorbent products for absorbing body fluids and, more particularly, to absorbent products having integral belts for retaining the absorbent product in a particular position.

BACKGROUND OF THE INVENTION

Absorbent products for absorbing body fluids must be retained in a position which brings the absorbent product into contact or within close proximity of the portion of the body from which the fluid to be absorbed emanates. For example, in the case of a sanitary napkin, it would be desirable to retain the absorbent product in the perineal area of the user.

Numerous techniques for fastening absorbent articles in place have been devised. The absorbent article is usually attached or affixed to the user's undergarment or other garment by either mechanical means, adhesive strips, or some combination thereof. Most of these methods suffer from the drawback of retaining the absorbent product in a fixed position relative to the garment. When the user moves, the garment may pull away from the body portion from which fluid is to be absorbed, thereby creating leakage and/or inefficient fluid collection. Moreover, none of the present attachment methods permit the user to comfortably and securely wear the absorbent product without the use of an undergarment.

It would therefore be desirable to provide means for attaching an absorbent article to the user in a secure fashion, while not inhibiting the conformance of the absorbent article to the user's body while they are undergoing routine motions. It would further be desirable to provide means for attaching an absorbent article directly to the user's body, obviating the need for an undergarment or other garment overlying the outward facing side of the absorbent product. Another advantage of such a system would be the elimination of adhesive attachment to the undergarment, thereby avoiding the need for release paper and additional waste disposal. Furthermore, such a system would eliminate the problem of the positioning adhesive attaching to itself during or prior to use.

SUMMARY OF THE INVENTION

Accordingly, it has now been found that absorbent products for absorbing body fluids may be provided which have conformable straps for retaining the absorbent product. In a preferred embodiment conformable straps are attached to each transverse end of an absorbent core. The conformable straps may be extended transversely to provide four strap ends which are extended around the body of the user and pairs of which are affixed together, preferably by knotting. The straps may also be affixed together by means of a slit system in which a slit is provided through which a ratcheted end is threaded. Buttons or VELCRO™ may be used for attachment, or a ring through which one strap may be threaded. This embodiment may be worn either with or without an undergarment or other garment. If a garment is worn, the attached pairs of straps preferably extend beyond the waistband of the garment and are retained thereby. As disclosed, it has now been found that conformable straps for retaining the absorbent product can be formed from a continuous sheet of conformable material. The material of the straps may either be attached to the garment facing surface of the absorbent article or a continuous sheet of conformable material may be affixed to the garment facing side, peripherally extending portions forming the conformable straps. Alternatively, embodiments are disclosed having straight longitudinally extending straps which are extended along the body of the user and folded over the waistband of a garment, thereby retaining the absorbent product in place.

The present invention also discloses methods of making absorbent products having integral conformable straps. The methods disclosed most preferably comprise cutting the conformable straps from a continuous sheet of material which has been affixed to the garment facing surface of the absorbent product.

DETAILED DESCRIPTION OF THE PREFERRED EMBODIMENTS

Figure 1:
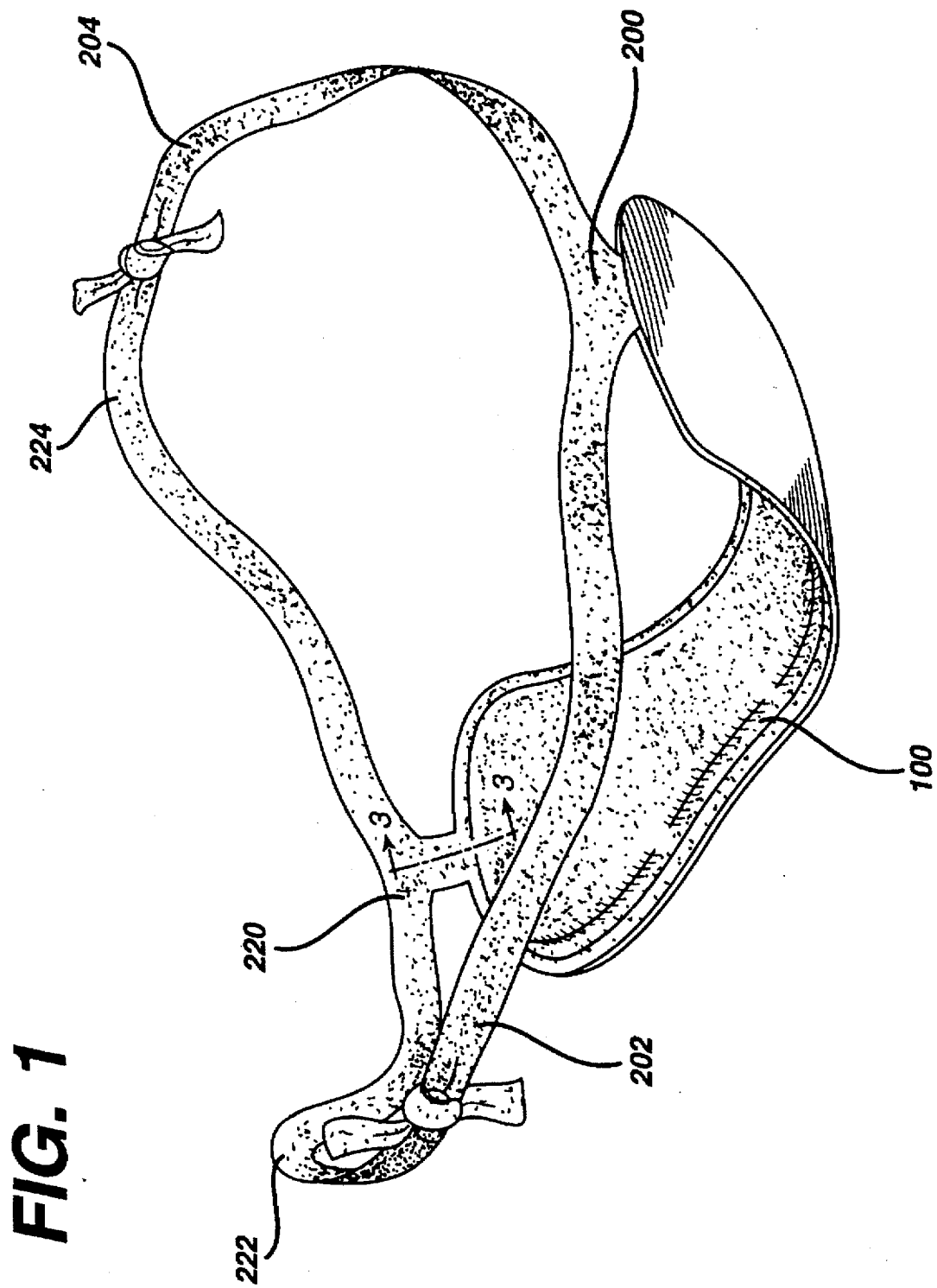
FIG. 1 is a perspective view of a most preferred embodiment of a sanitary napkin made in accordance with the present invention.

As depicted in FIG. 1, a most preferred embodiment of the present invention comprises an absorbent product, such as a sanitary napkin 100 from which two conformable straps 200, 220 extend from each transverse end of the product. As shown, the straps 200, 220 extend longitudinally for a short distance and then continue to extend transversely, thereby forming four individual strap ends 202, 204, 222, 224.

In FIG. 1, these strap ends, 202, 204, 222, 224 are shown in the general shape they will take when applied to the body of a user. However, neither the user nor an undergarment is illustrated. It will be observed that a first paid of strap ends 202, 222, and a second pair of ends 204, 224 are affixed to each other to create a means for holding the absorbent product in place. Most preferably, the ends 202, 204, 222, 224 are simply knotted together. However, as will be understood by those of ordinary skill, numerous other fastening methods will also provide useful embodiments. For example, adhesive tabs, VELCRO™ type-fastening systems, snaps, pins or other forms of fasteners may all be provided to affix the distal ends of each pair of strap ends 202, 222, 204, 224 to one another.

Figure 2:
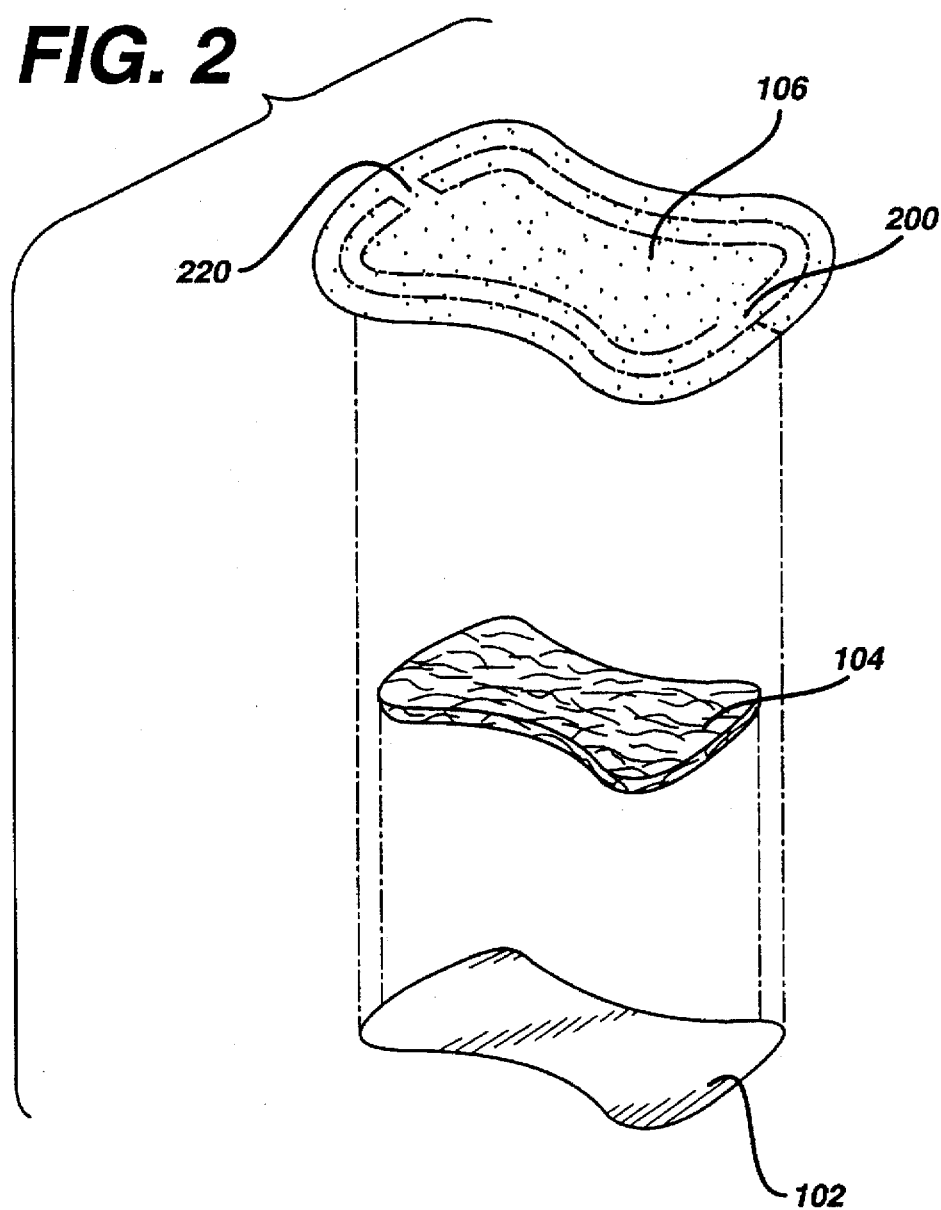
FIG. 2 is an exploded perspective view of the construction of the absorbent article depicted in FIG. 1.

Referring now to FIG. 2, an advantageous and preferred method of constructing the absorbent article of FIG. 1 is shown as an exploded view. The absorbent article, for example a sanitary napkin 100, is typically comprised of a body facing, fluid permeable top sheet 102 which overlies an absorbent core 104. As will be understood by those of ordinary skill, the absorbent core 104 may be comprised of one or more layers of absorbent material, as well as other materials, fillers, binders, etc. which perform the absorptive and retentive functions normally associated with this type of product. Overlying the side of the absorbent core 104, opposite the top sheet 102, is an outward facing backing sheet 106. As explained below and shown here, the conformable straps 200, 220 discussed above with reference to FIG. 1 are shown prior to their application. Thus, the straps 200, 220 are integral with the rest of the backing sheet 106, however, they are easily separated along pre-formed slits, perforations or other formed tear lines. Straps 200, 220 may be composed of nonwoven materials, elasticized materials, woven cloth or polymer films or the like. Generally, any soft, drapable or flexible material may be used for the purpose of forming straps.

Figure 3:
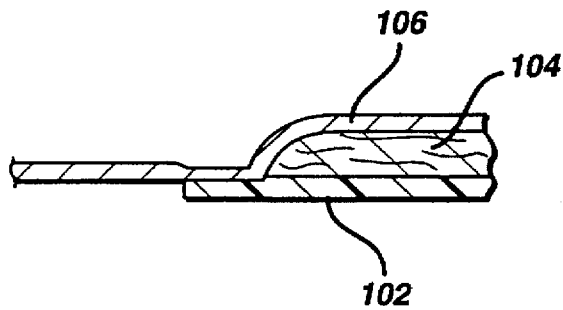
FIG. 3 is a partial cross-sectional view taken along line 3—3 in FIG. 1.
Figure 4:
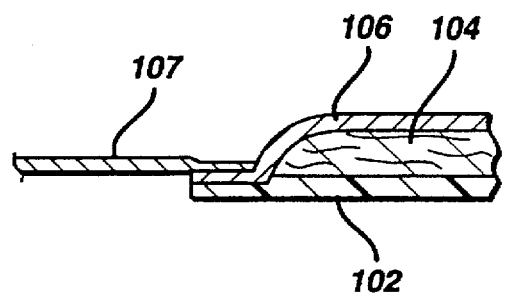
FIG. 4 is an alternate construction of the cross-section depicted in FIG. 3.

FIG. 3 and FIG. 4 illustrate alternate embodiments of the embodiment of the present invention depicted in FIG. 1, taken along line 3—3 thereof. In the first alternate construction shown in FIG. 3, the backing sheet 106 simply overlies the absorbent core 104 and is attached to the top sheet 102 by heat sealing, adhesives or other means. it should be noted that top sheet 102 extends beyond the periphery of the absorbent core 104 for this purpose.

Alternatively, as shown in FIG. 4, the backing sheet 106 and the top sheet 102 are attached to form a common continuous edge which extends beyond the peripheral edge of the absorbent core 104. Along the edge formed, an additional cover sheet portion 107 is affixed to the backing sheet 106. The additional backing sheet portion thus extends around the periphery of the edge formed between the top sheet 102 and the backing sheet 106, and is substantially comprised of the conformable straps 200, 220. Thus, the resulting joined backing sheet portions 106, 107 are similar to the backing sheet 106 shown in FIG. 2, except that an additional seam is created where they are joined. An advantage of the construction depicted in FIG. 4 is that it can be adapted for use in conjunction with existing absorbent product designs and the equipment for making them. Thus, production efficiency is increased by reducing re-tooling time and cost.

Figure 5:
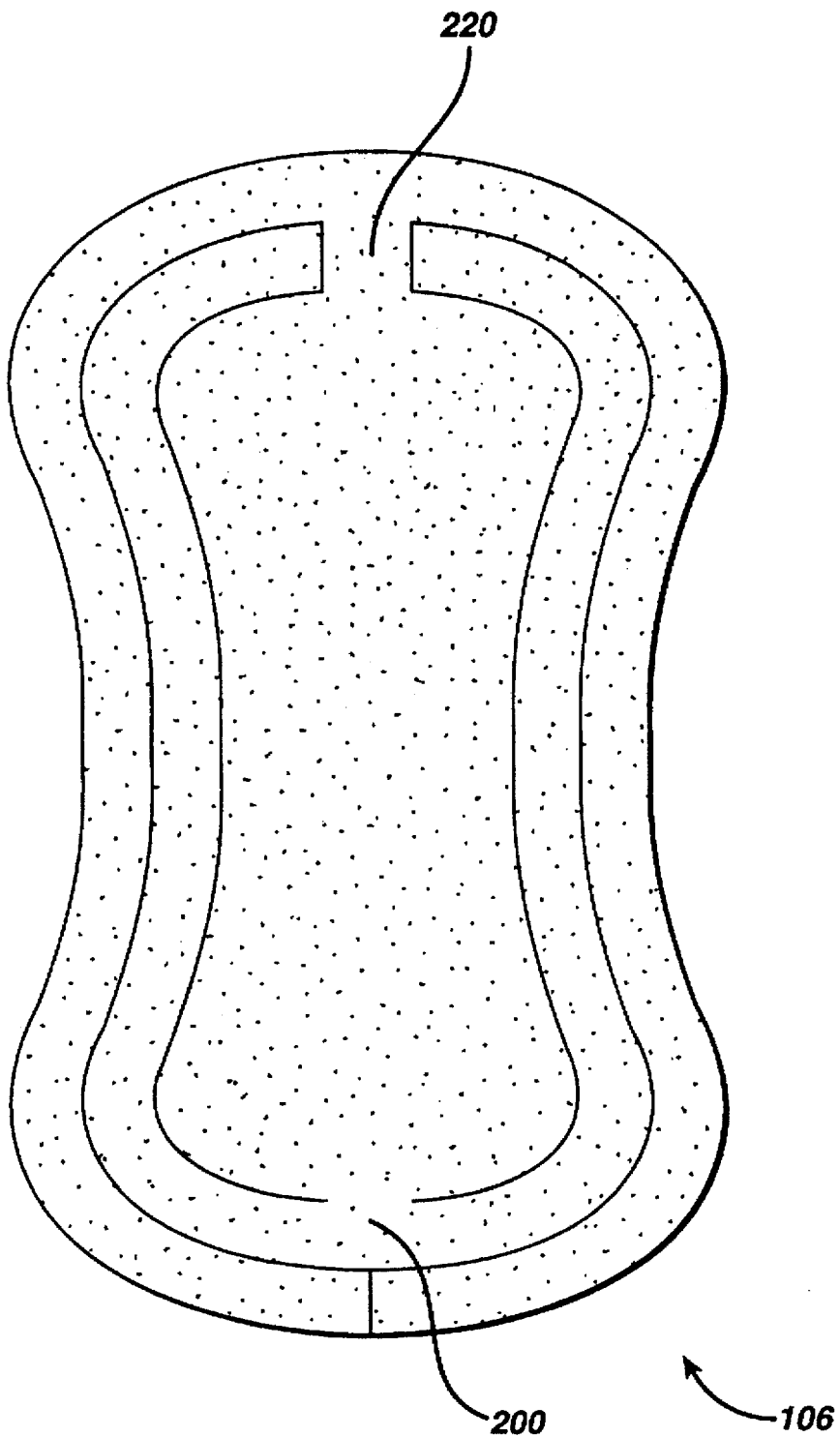
FIG. 5 is a plan view of the outward facing side of the absorbent article depicted in FIG. 1, prior to its application.

Turning now to FIG. 5 a plan view of the cover sheet described above is shown in full plan view. It can be seen how, in a most preferred embodiment, the cover sheet 106 can be cut, perforated or otherwise prepared in a manner which allows the conformable straps 200, 220 to be formed from a continuous piece of material. Although solid lines are shown defining the conformable straps 200, 220, it will be understood by those of ordinary skill that, as mentioned above, perforations or other means permitting the separation of the straps 200, 220 from the remainder of the cover sheet by the user just prior to application.

Figure 6:
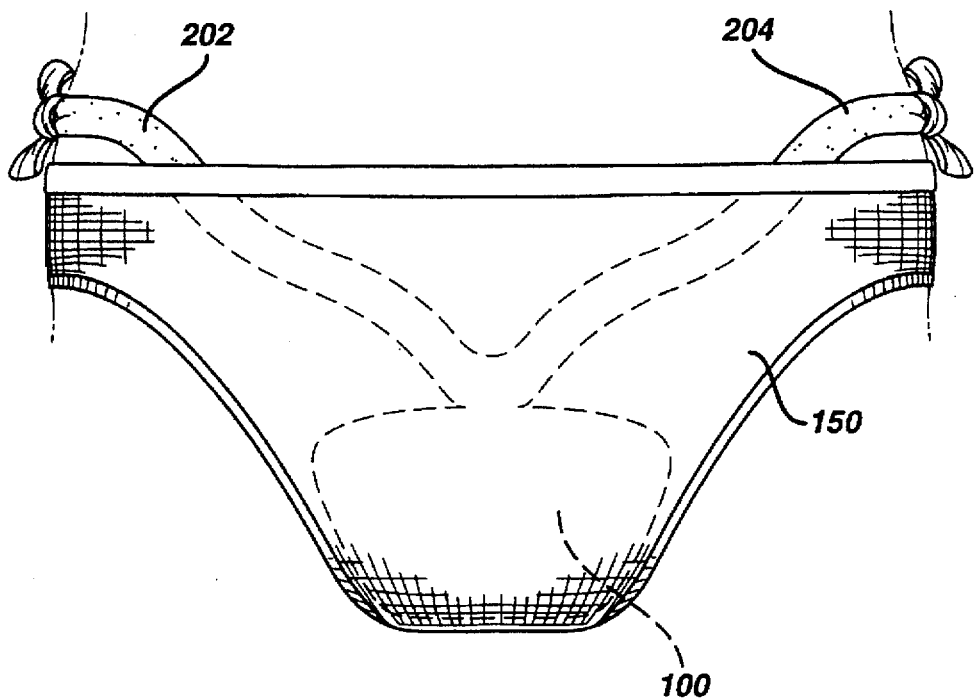
FIG. 6 is a frontal view of the placement of the absorbent article depicted in FIG. 1 on a user.

The positioning of the preferred embodiment of the present invention described in FIGS. 1–5 in relation to the undergarment of the user is shown in FIG. 6. Although it may be feasible in some circumstances to wear the sanitary napkin 100 without an overlying undergarment, most preferably an undergarment 150 is worn. FIG. 6 depicts a frontal view of a pair of panties 150 and shows the sanitary napkin primarily in phantom. A pair of strap ends 202, 204 are extended upwardly and around the body of the user, preferably, although not necessarily, in a position where their distal ends extend beyond the waistband of the undergarment 150. The attachment means, e.g., the knot, prevents the belt from sliding down the body. It will be observed that the strap ends 202, 204 take on a somewhat convoluted shape, due to the shape of the cover sheet and the manner in which they are formed. In other embodiments which use separate conformable straps, strings, bands or the like, which are preferably attached in the manner illustrated in FIG. 4, the degree of such convolution may vary.

Figure 7:
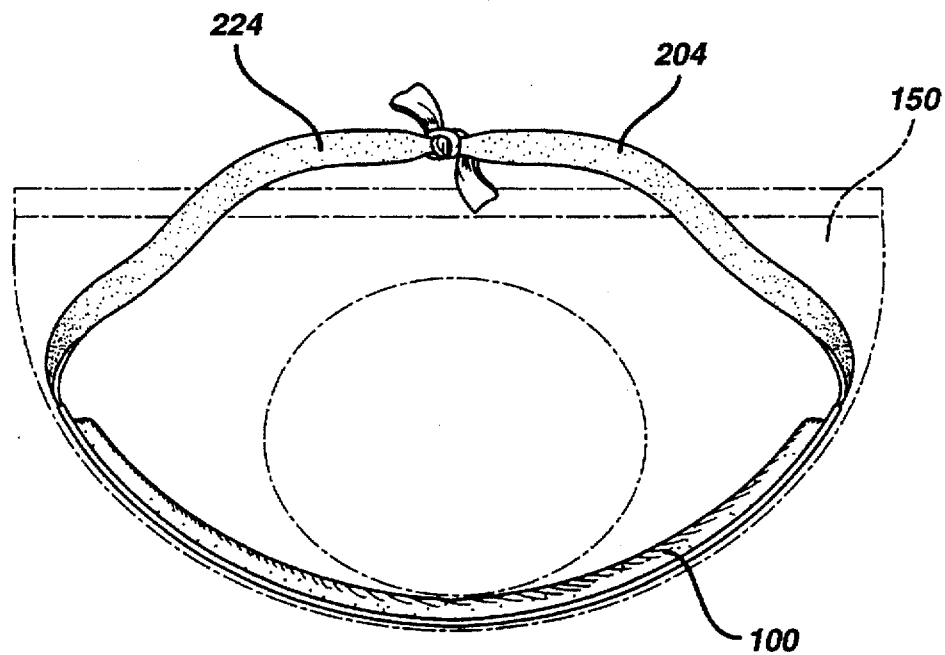
FIG. 7 is a side view of FIG. 6, with the user's undergarment shown in phantom.

A side view of the preferred embodiment of the present invention depicted in FIG. 6 is shown in FIG. 7. In this view, the undergarment 150 is shown in phantom, while the sanitary napkin 100 is fully visible. The pair of strap ends 204, 224 are brought together and most preferably are tied in a knot along the side of the user's hip, above the waistline of the undergarment.

Figure 8:
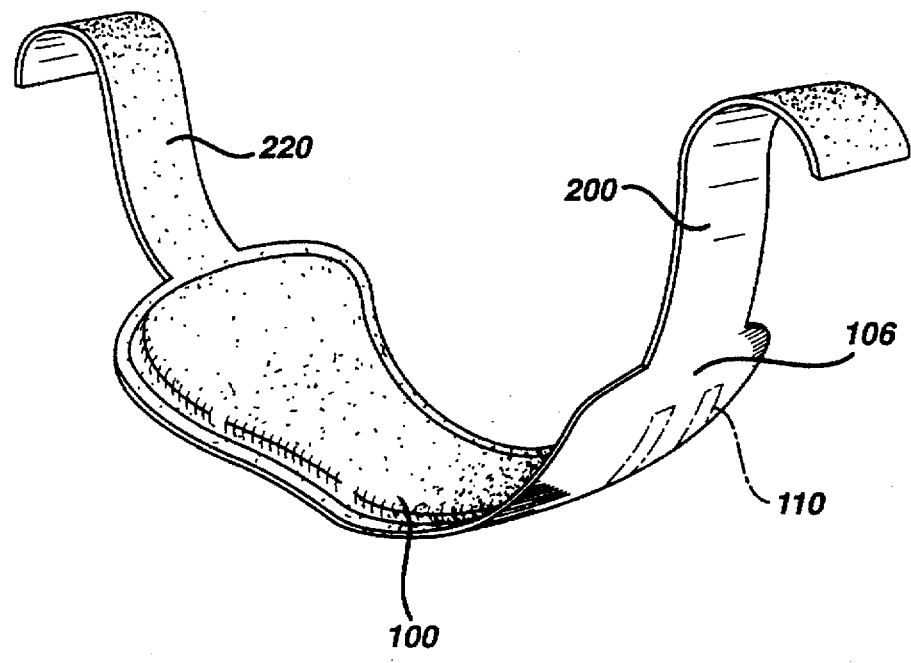
FIG. 8 is a perspective view of an alternate embodiment of the present invention, shown in position for use.
Figure 9:
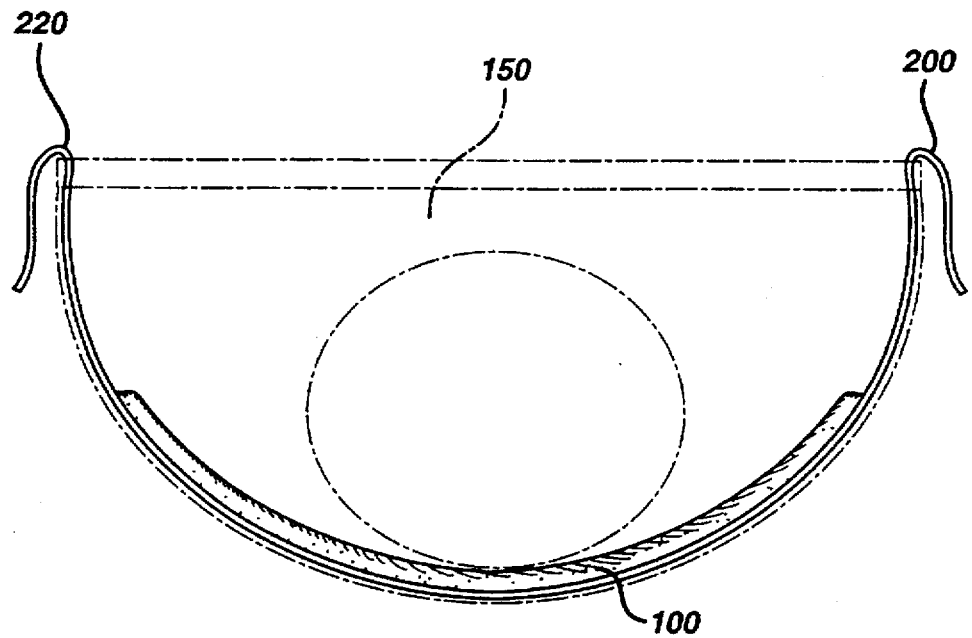
FIG. 9 is a side view of the embodiment of FIG. 8, showing the application of the present invention to the user's body, similar to FIG. 7.

An alternative embodiment of the present invention is depicted in FIGS. 8–9. In FIG. 8, a perspective view of a sanitary napkin 100 made in accordance with the present invention is shown. Longitudinally extending conformable straps 200, 220 are again provided. However, in this embodiment the straps 200, 220 extend in the longitudinal direction from each transverse end of the product by a sufficient amount to extend beyond the waist band of an undergarment. In addition to being retained by the distal ends of the conformable straps 200, 220 which are engaged with the waistband of an undergarment, one or more adhesive strips 110 may also be provided. The strips 110 are disposed on the garment facing, outward surface of the cover sheet 106.

Referring now to FIG. 9, the application of the sanitary napkin 100 shown in FIG. 8 is depicted in a side view. An undergarment 150 is shown in phantom. It will be observed that the conformable straps 200, 220 extend from the sanitary napkin 100, beyond the waistband of the undergarment 150 and are folded or draped over the waistband, thus securing the absorbent product in place.

Although certain embodiments of the present invention have been set forth and described above, the present invention is not so limited. Numerous variations and modifications to the embodiments disclosed are contemplated. Moreover, the present invention will find application in a wide variety of absorbent products and applications of those products. For example, incontinence pads and other similar absorbent pads may be worn in the manner disclosed by the present invention. Accordingly, reference should be made to the appended claims in order to determine the scope of the present invention.

We claim:

1. An absorbent product wearable about a user's body for absorbing body fluids comprising: an absorbent core having a body facing side, a garment facing side, lateral sides and transverse ends; and a sheet of material affixed to and extending beyond the lateral sides and the transverse ends of the absorbent core to form a peripheral extension, wherein conformable straps for retaining the body facing side of the absorbent core in a perineal region of a user are defined by a plurality of perforated lines, are formed using substantially all of the peripheral extension, are affixed to each transverse end of the absorbent core, each of the straps forms two strap ends extendable around a portion of the user's body, each of the strap ends having a distal end attachable to another strap end, thereby affixing the absorbent core in the perineal area of the user by encircling a portion of the user's body.

2. The absorbent product of claim 1, worn about a user's body, wherein each strap end has a length which is at least as long as a corresponding lateral edge of the absorbent core.

3. The absorbent product of claim 2, wherein the sheet of material substantially covers the garment facing side of the absorbent core.

4. The absorbent product of claim 2, wherein the distal ends of the straps are attached to each other by means for fastening.

5. The absorbent product of claim 4, wherein the distal ends of the straps are attached by knotting.

6. The absorbent product of claim 4, wherein the distal ends of the straps are attached by adhesive means.

7. The absorbent product of claim 1, wherein the absorbent product is a sanitary napkin.

8. The absorbent product of claim 1, wherein the absorbent product is an incontinency pad.

9. The absorbent product of claim 1, wherein the plurality of perforated lines defines a pair of conformable straps.

* * * * *